United States Patent
Colleran et al.

[11] Patent Number: 5,871,546
[45] Date of Patent: Feb. 16, 1999

[54] FEMORAL COMPONENT CONDYLE DESIGN FOR KNEE PROSTHESIS

[75] Inventors: Dennis P. Colleran, Plainville; Stefan M. Gabriel, Lakeville; Jorge A. Ochoa; Robert E. Sommerich, both of Norton, all of Mass.

[73] Assignee: Johnson & Johnson Professional, Inc., Raynham, Mass.

[21] Appl. No.: 537,241

[22] Filed: Sep. 29, 1995

[51] Int. Cl.⁶ .................................................. A61F 2/38
[52] U.S. Cl. ............................................... 623/20; 623/18
[58] Field of Search ................... 623/16, 18–22, 623/39

[56] References Cited

U.S. PATENT DOCUMENTS

| | | | |
|---|---|---|---|
| Re. 29,757 | 9/1978 | Helfet | 3/1.91 |
| 4,081,866 | 4/1978 | Upshaw et al. | 623/20 |
| 4,470,158 | 9/1984 | Pappas et al. | 623/18 |
| 4,714,472 | 12/1987 | Averill et al. | 623/20 |
| 4,888,021 | 12/1989 | Forte et al. | 623/20 |
| 4,950,298 | 8/1990 | Gustilo et al. | 623/20 |
| 5,007,933 | 4/1991 | Sidebotham et al. | 623/20 |
| 5,171,276 | 12/1992 | Caspari et al. | 623/16 |
| 5,197,987 | 3/1993 | Koch et al. | 623/20 |
| 5,201,768 | 4/1993 | Caspari et al. | 623/20 |
| 5,203,807 | 4/1993 | Evans et al. | 623/20 |
| 5,219,362 | 6/1993 | Tuke et al. | 623/18 |
| 5,236,461 | 8/1993 | Forte | 623/20 |
| 5,326,361 | 7/1994 | Hollister | 623/20 |
| 5,330,534 | 7/1994 | Herrington et al. | 623/20 |
| 5,358,529 | 10/1994 | Davidson | 623/18 |
| 5,370,699 | 12/1994 | Hood et al. | 623/20 |
| 5,387,240 | 2/1995 | Pottenger et al. | 623/20 |
| 5,507,820 | 4/1996 | Pappas | 623/20 |

*Primary Examiner*—John G. Weiss
*Assistant Examiner*—Francis K. Cuddihy
*Attorney, Agent, or Firm*—Nutter, McClennen & Fish, LLP

[57] ABSTRACT

A knee joint prosthesis includes a femoral component, a tibial plateau, and a tibial bearing member. The design and geometry of the articulation surfaces of the condylar elements of the femoral component and tibial bearing member is such that contact area between the articulation surfaces is maximized during flexion of the prosthesis. This is achieved by increasing the coronal radius of the bearing surfaces of the femoral component in the anterior to posterior direction along the bearing surface, i.e., increasing the coronal radius of the bearing surfaces of the femoral component as the femoral component transitions from extension to flexion.

14 Claims, 7 Drawing Sheets

FEMORAL COMPONENT CONDYLE DESIGN FOR KNEE PROSTHESIS

BACKGROUND OF THE INVENTION

This invention relates to implantable bone prostheses, and more particularly to knee joint prostheses.

Joint replacement surgery is quite common and enables many individuals to function normally when otherwise it would not be possible to do so. Artificial joints are normally composed of metallic, ceramic and/or plastic components that are fixed to existing bone.

Knee arthroplasty is a well known surgical procedure by which a diseased and/or damaged natural knee joint is replaced with a prosthetic knee joint. Typical knee prostheses include a femoral component, a patella component, a tibial tray or plateau, and a tibial bearing member. The femoral component generally includes a pair of laterally spaced apart condylar portions, the distal surfaces of which articulate with complementary condylar elements formed in a tibial bearing component.

In a properly functioning artificial knee joint, the condylar portions of the femoral component must slide and roll freely over the articulation surface formed by the condylar elements of the tibial bearing member. Natural friction within a replaced, artificial joint can lead to the development of wear debris in which minute particles of debris (e.g., metal or plastic from the prosthesis) become dislodged and migrate within the joint. The phenomenon of wear debris within artificial joints is a serious problem that can inhibit the proper mechanical functioning of the joint. Moreover, wear debris can lead to osteolysis and bone deterioration. When wear debris develops within an artificial joint, surgical removal of the debris or subsequent replacement of the artificial joint is often necessary.

During normal usage of a properly implanted prosthetic knee joint, load and stress are placed on the tibial bearing member. The tibial bearing member is typically made of an ultrahigh molecular weight polyethylene (UHMWPE). Friction, continuous cycling and stress can cause some erosion and/or fracture of the tibial bearing member, thus leading to wear debris. The risk of wear debris can be even greater during malalignment of an artificial knee joint, which can result from normal usage or from imperfect and/or inaccurate implantation of the prosthesis within a patient. As a result of malalignment, the load upon the tibial bearing member is not evenly distributed. Instead, excess load is placed on certain areas of the tibial bearing member. This uneven distribution of load (or edge loading) can accelerate the development of wear debris. Contact stresses on the tibial bearing member increase substantially with malalignment of the joint, thus increasing the risk that wear debris will develop when a prosthetic knee joint is subjected to malalignment conditions.

Contact stresses on the tibial bearing member also tend to increase when the prosthetic knee joint is rotated into flexion. This increased contact stress results from a corresponding decrease in tibio-femoral contact area.

There is thus a need for knee joint prostheses that have reduced tendency to develop wear debris due to the maintenance of good contact area and low contact stress between femoral and tibial components, even during the dynamics of daily activity and in various conditions of flexion and malalignment.

Accordingly, it is an object of the present invention to provide knee joint prostheses with improved performance and a longer use for life. It is also an object of the invention to provide knee joint prostheses having reduced tendency to develop wear debris. A further object of the invention is to provide knee joint prostheses which are able to maintain relatively high contact area and low contact stress between femoral and tibial components throughout the normal range of motion and in conditions at malalignment. Another object of the invention is to provide knee joint prostheses that exhibit acceptable levels of laxity despite maintaining good tibio-femoral contact area in conditions of flexion. These and other objects will be apparent from the description that follows.

SUMMARY OF THE INVENTION

The invention provides a knee joint prosthesis in which the articulation surfaces of the femoral and tibial components are configured to maintain good contact area and low contact stress when implanted in a patient. The femoral component of the knee joint prosthesis has a proximal surface which is mountable on a distal end of the femur of a patient, and a distal articulation surface. Preferably the distal articulation surface includes two adjacent, semi-parallel bearing surfaces that form femoral condyles. Each femoral condyle is of a curved, convex shape in both the anterior-posterior direction and in the medial-lateral direction. The curvature of each femoral condyle lying in the sagittal plane, in contact with a tibial condylar element, and extending in the anterior-posterior direction is defined by at least two semi-parallel radii wherein a first sagittal radius is more anterior than a second sagittal radius. The first and second sagittal radii are offset from one another by the distance between their respective centers of curvature. Preferably, the centers of curvature of the first and second sagittal radii are coplanar.

The curvature of each femoral condyle lying in the coronal plane, in contact with a tibial condylar element, and extending in the medial-lateral direction is defined by multiple coronal radii. The coronal radii increase in value from a minimum value at an anterior portion of the bearing surface, corresponding to about 0° flexion, to a maximum value at a posterior portion of the bearing surface corresponding to about 60° to 90° flexion.

The coronal radius is approximately 0.7 to 1.1 inches at its minimum value at an anterior portion of bearing surface, and it increases to a maximum value of about 0.74 to 1.17 inches at a posterior portion of the bearing surface corresponding to about 60° to 90° flexion. Alternatively, the maximum value of the coronal radius of the femoral condyles can be approximately equal to, but not greater than, the coronal radius of the tibial insert which the femoral condyles contact. The coronal radius remains substantially constant at portions of the bearing surface posterior of the maximum radius value.

The prosthesis also includes a tibial tray or plateau having a proximal end and a distal end that is mountable on the tibia of the patient. Further, the prosthesis includes a tibial bearing member having a proximal articulation surface and a distal surface that is mountable within the proximal end of the tibial plateau component. The proximal articulation surface of the tibial bearing member includes two adjacent tibial condylar elements that seat the adjacent, semi-parallel bearing surfaces of the femoral component. Each condylar element of the tibial bearing member is of a curved, concave shape in both the anterior-posterior and medial-lateral directions.

The prosthesis of the present invention is characterized by improved contact between the femoral condyles and the tibial condylar elements. That is, in conditions of flexion, the tibio-femoral contact area remains approximately equal to the contact area at zero flexion, or the contact area only decreases to an extent less than that typically expected in a knee joint prosthesis. Preferably, contact area between the condyles of the femoral component and the condylar elements of the tibial bearing member, at 0° flexion and without malalignment, is in the range of 200 to 400 mm$^2$, and typically is about 270 mm$^2$. Preferably the tibio-femoral contact area remains substantially the same throughout the range of motion. Typical existing knee prostheses produce a tibio-femoral contact area decrease of about 100 to 200 mm$^2$ at 60°–90° flexion. The ability to achieve substantially the same tibio-femoral contact area after flexion represents an improvement over many current femoral component designs in which the contact area at 90° flexion drops to about 130 mm$^2$ or less. Such improved contact area at higher degrees of flexion, as compared to other femoral component designs, reduces the magnitude of contact stresses that are generated at higher degrees of flexion. The present design should therefore result in a reduced tendency to develop wear debris and thus a longer lifetime for the prosthetic joint.

DETAILED DESCRIPTION OF THE INVENTION

The present invention provides an improved construction for knee joint prostheses, especially as the femoral component rotates into flexion. The design and geometry of the knee joint prosthesis of the invention facilitate greater contact between the femoral and tibial components of the knee joint prosthesis during flexion than that which is typically associated with knee prostheses.

Figure 1:
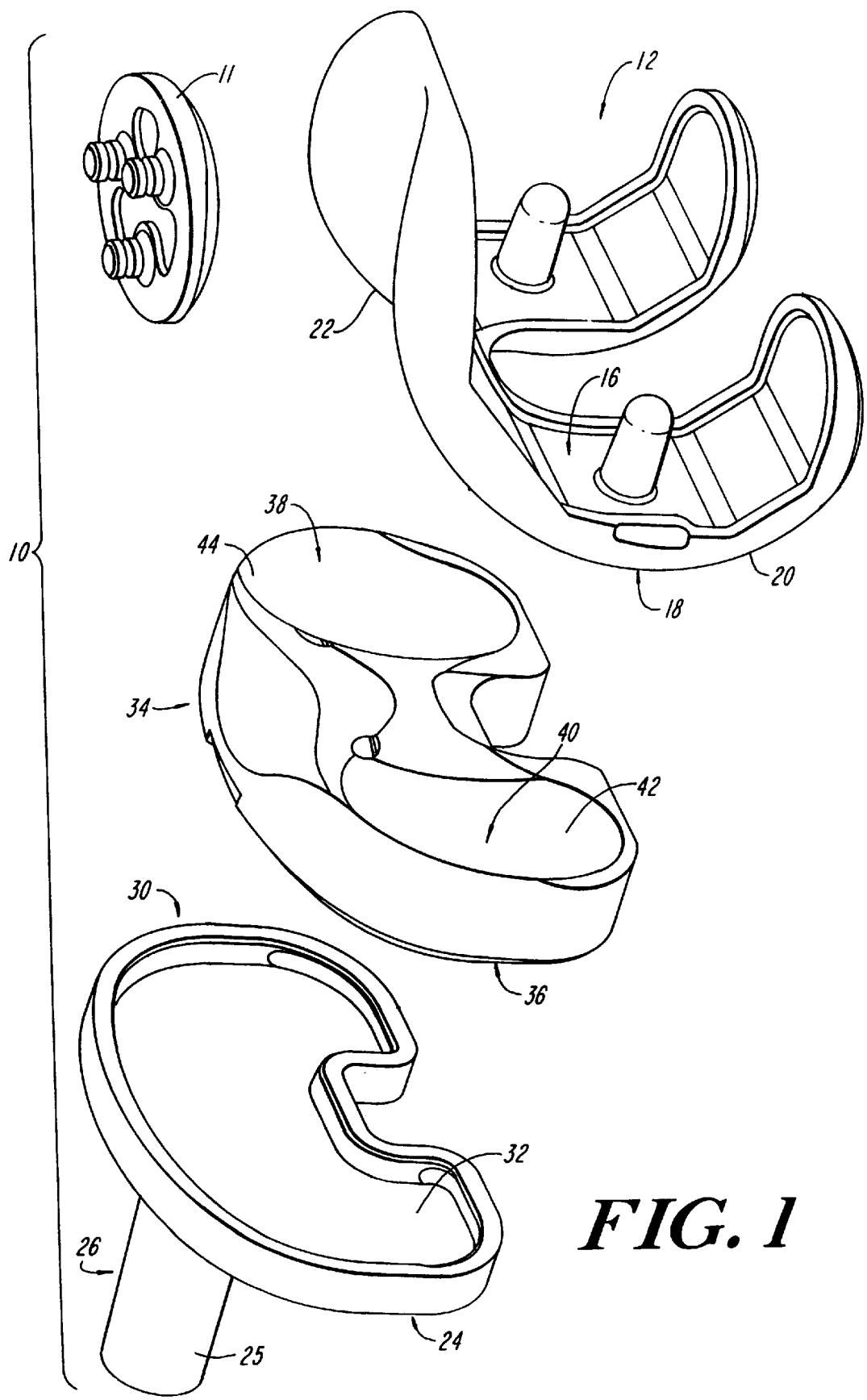
FIG. 1 is an exploded, perspective view of an artificial knee joint illustrating the femoral component, the patella component, the tibial bearing member and the tibial plateau.
Figure 2:
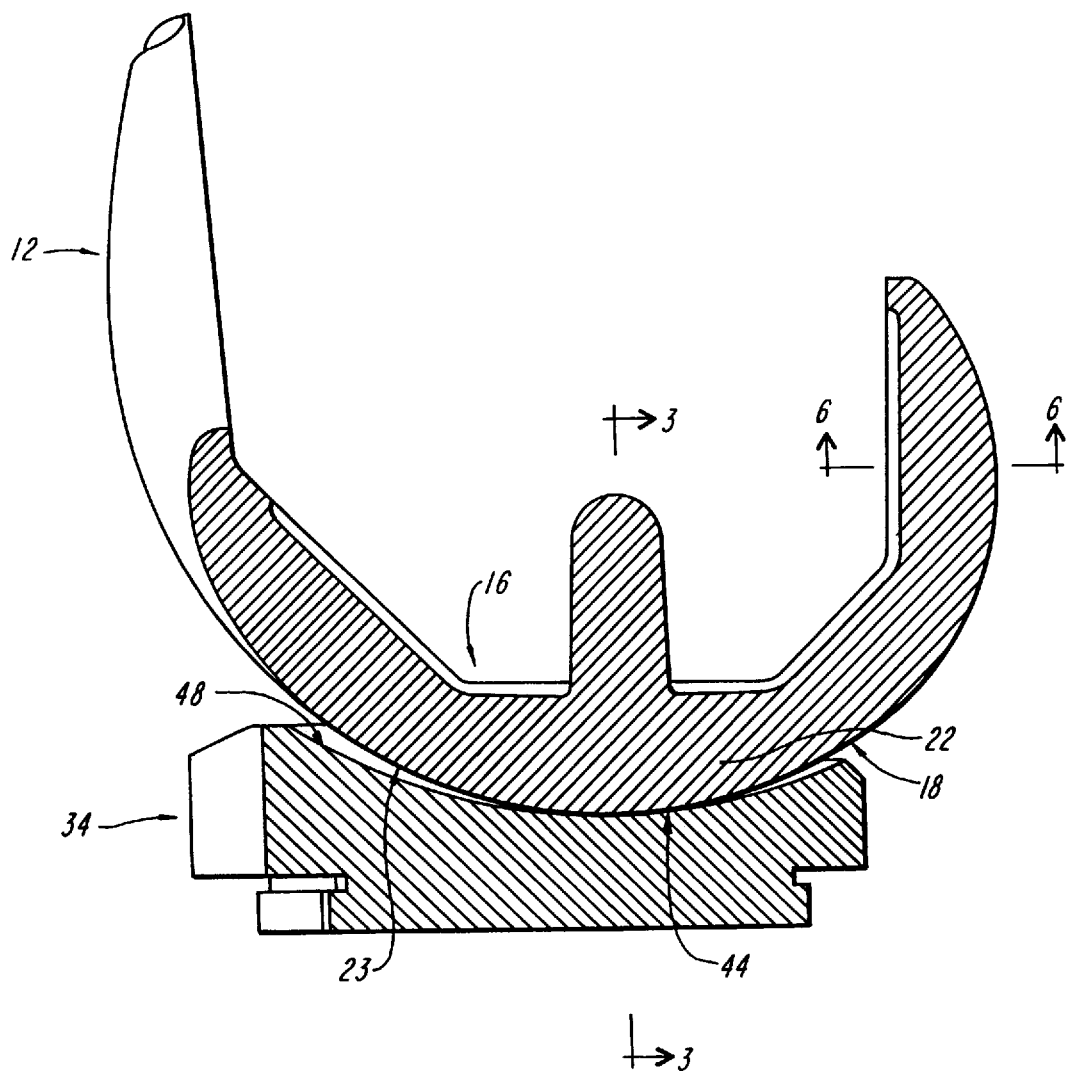
FIG. 2 is a side view from the medial side, with cross-section, of an artificial knee femoral component positioned adjacent a prosthetic tibial bearing member in perfect alignment and at 0° flexion.

FIG. 1 illustrates four components found in a knee joint prosthesis 10 constructed according to the present invention. A patella component 11 is adapted to seat against an anterior portion of the femoral component 12. The femoral component 12 includes an inferior surface 16 which is mountable within the distal end of a patient's femur and a superior articulation surface 18. The articulation surface 18 includes adjacent lateral 20 and medial 22 condyles. The knee prosthesis 10 also includes a tibial tray or plateau 24, the distal end 26 of which includes a distally extending stem 25 which is mountable within the tibia of a patient. The proximal end 30 of the tibial plateau includes a recessed region 32 within which a tibial bearing member 34 is mounted in a mechanical fit.

Figure 3:
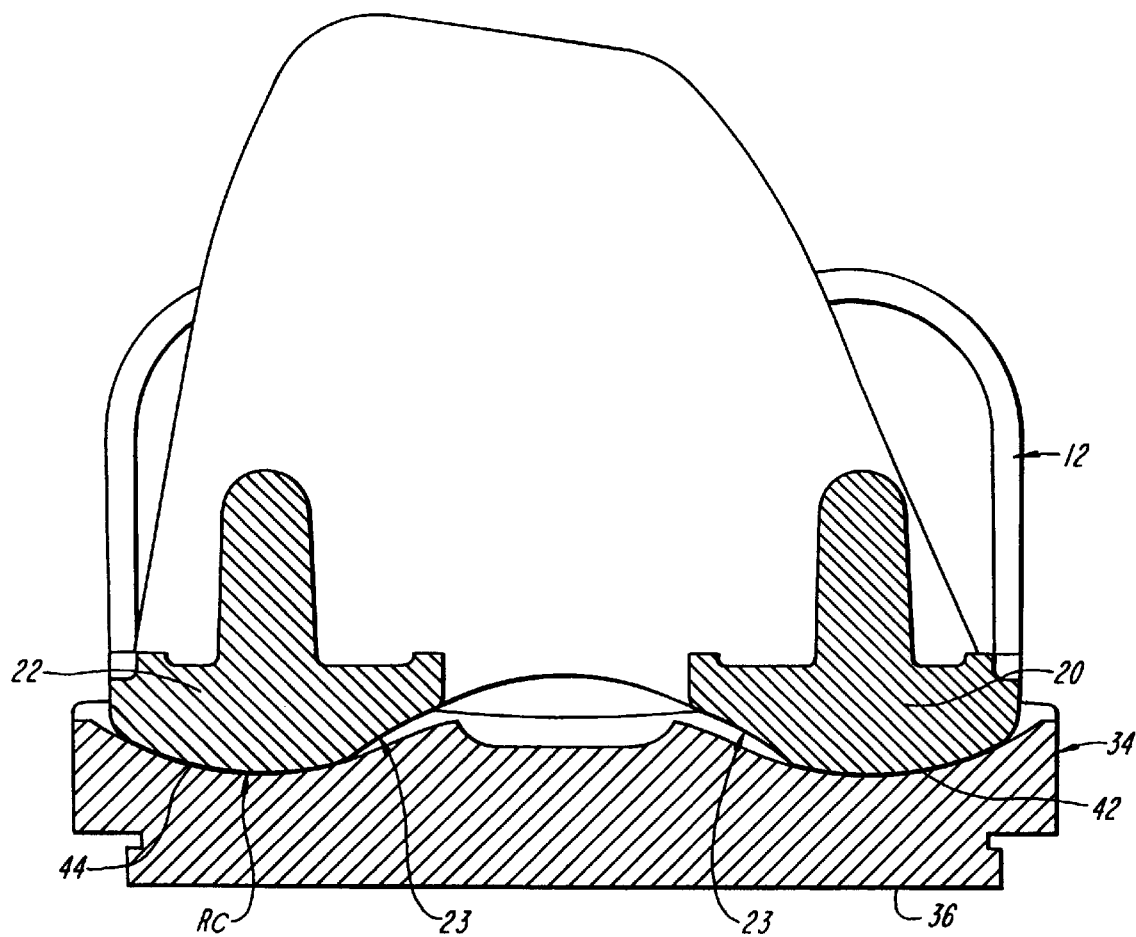
FIG. 3 is an anterior view, with cross-section at lines 3—3, of the artificial knee femoral component shown in FIG. 2 positioned adjacent a prosthetic tibial bearing member in a condition of perfect alignment and at 0° flexion.
Figure 4:
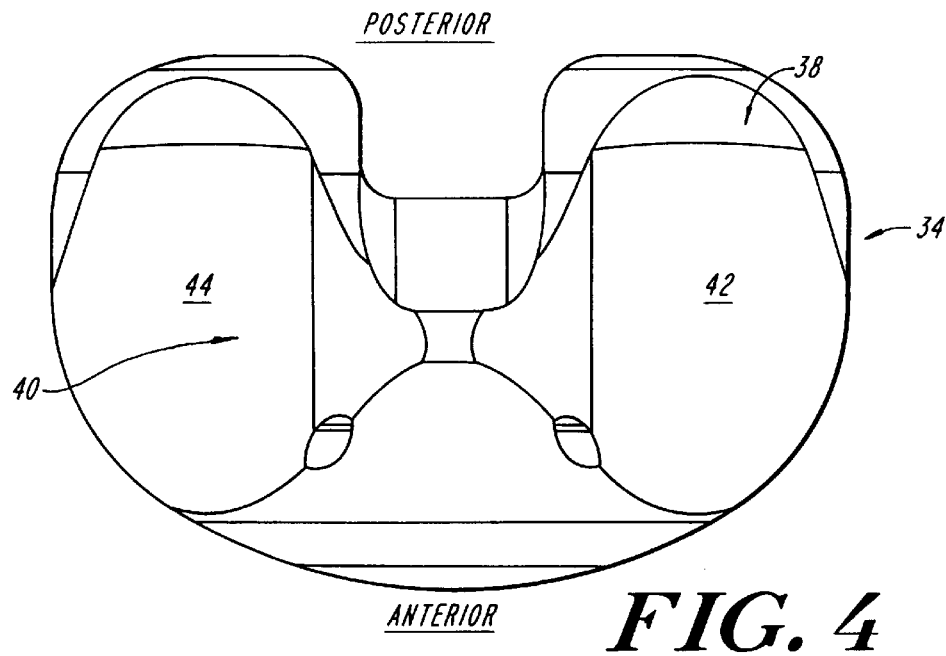
FIG. 4 is a top view of the prosthetic tibial bearing member shown in FIG. 1.

Tibial bearing member 34 includes a distal surface 36 mountable within a recessed region 32 of proximal end 30 of tibial plateau 24. The proximal surface 38 of tibial bearing member 34 forms an articulation surface 40 that engages and articulates with the articulation surface 18 of femoral component 12. The articulation surface 40 of the tibial bearing member 34 includes adjacent lateral 42 and medial 44 condyles. As shown in FIG. 3, the lateral and medial condyles 20, 22 of the femoral component 12 mount in engagement with the lateral and medial condyles 42, 44 of tibial bearing member 34.

Although not illustrated, it is understood that a tibial component of an artificial knee joint can be formed as a single piece which includes portions that correspond to tibial tray component 24 and tibial bearing member 34. Typically, such single piece units are manufactured of ultrahigh molecular weight polyethylene.

The condyles 20, 22 of femoral component 12 and the condyles 42, 44 of tibial bearing member 34 are configured such that a relatively large contact area is achieved when the condyles of the femoral component and the condyles of the tibial bearing member engage each other. Greatest contact area is achieved in conditions of perfect alignment, throughout the range of motion of the knee joint. In conditions of malalignment, including varus-valgus lift and internal-external rotation, contact area of existing knee prostheses typically decreases substantially. The term "perfect alignment", as used herein refers to a condition where the knee joint is subjected to 0° varus-valgus lift, and 0° internal-external rotation throughout the anatomic range of flexion-extension (i.e., about −10° to 120°).

Figure 5:
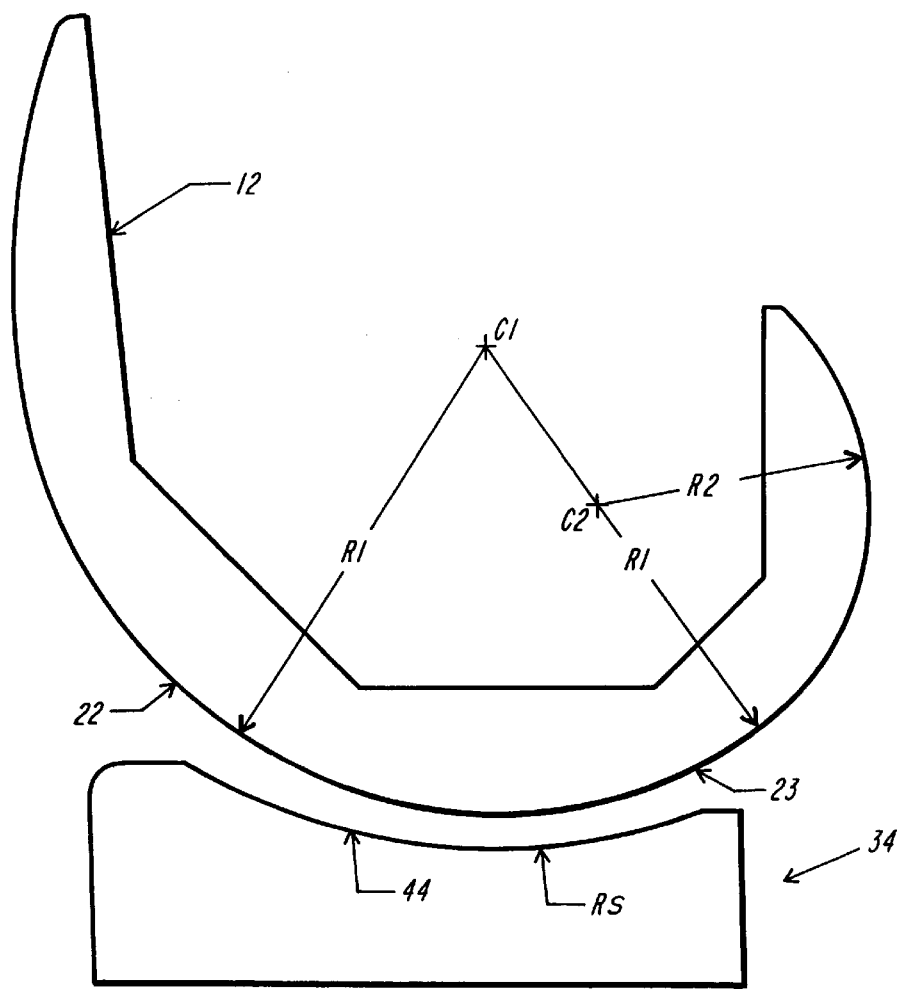
FIG. 5 is a sectional view, in the sagittal plane, of a femoral component and tibial bearing member constructed according to the present invention.

FIGS. 2 through 7 illustrate the femoral component 12 of the invention, including condyles 20, 22. Each condyle 20, 22 is generally ellipsoid in shape and is of a curved, convex shape in both the anterior-posterior direction and in the medial-lateral direction. In a preferred embodiment, the curvature of the articulation surface 23 of each condyle 20, 22 lying in the sagittal plane, in contact with the condyles 42, 44 tibial bearing member, and extending in the anterior-posterior direction is defined by at least two semi-parallel radii wherein a first sagittal radius is more anterior than a second sagittal radius. The first, more anterior sagittal radius ($R_1$) is offset from the second sagittal radius ($R_2$) by the distance between their respective centers of curvature ($C_1$, $C_2$). As shown in FIG. 5, the curvature of the articulation surface 23 lying in the sagittal plane for each condyle 20, 22 can be defined by approximately 4 radii. However, the critical surface geometry is that which relates to the portion of the condyles 20, 22 which contact the condyles 42, 44 of the tibial bearing member 34. A first sagittal radius ($R_1$) covers an intermediate portion of the articulation surface 23 of each condyle 20, 22 in the sagittal plane and extending in the anterior-posterior direction. Typically, the articulation surface 23 of condyles 20, 22 defined by the first sagittal radius ($R_1$) contacts the articulation surface 40 of tibial bearing member 34 during flexion of the knee between approximately 0° and 40°. The first sagittal radius ($R_1$) is in the range of approximately 1.020 to 1.885 inches.

The second sagittal radius ($R_2$) covers a more posterior portion of the articulation surface 23 of condyles 20, 22 lying in the sagittal plane and extending in the anterior-posterior direction. The articulation surface 23 of condyles 20, 22 defined by $R_2$ typically contacts the articulation surface 40 of tibial bearing member 34 during flexion of the knee greater than about 400. The second sagittal radius ($R_2$) preferably has a value of approximately 0.6 to 1.2 inches, and more preferably due to anatomic constraints, a value of about 0.7 to 1.1 inches.

As illustrated in FIG. 5, the first and second sagittal radii ($R_1$, $R_2$) originate from their respective centers of curvature ($C_1$, $C_2$). The centers of curvature $C_1$ and $C_2$ are collinear and the center of curvature for $R_2$ ($C_2$) is more posterior than the center of curvature for $R_1$ ($C_1$).

The values of the first and second sagittal radii ($R_1$, $R_2$) are, to some extent, dependent upon the size of the femoral component. Typically, femoral components are available in different sizes to accommodate the anatomies of different patients. Femoral components can have dimensions in which the largest width (in the anterior-posterior dimensional ranges from about 50 to 74 mm, and in which the largest width (in the medial-lateral dimension) ranges from about 54 to 78 mm. Table 1 illustrates approximate values for the first and second sagittal radii with varying femoral component sizes.

TABLE 1

| Femoral Component Size | A-P Width (mm) | M-L Width (mm) | $R_1$ Value (inches) | $R_2$ Value (inches) |
|---|---|---|---|---|
| 2 | 56 | 60 | 1.194 | 0.743 |
| 3 | 61 | 66 | 1.321 | 0.794 |
| 4 | 65 | 71 | 1.405 | 0.828 |
| 5 | 69 | 73 | 1.511 | 0.860 |
| 6 | 74 | 78 | 1.750 | 0.950 |

Usually, as a prosthetic knee joint goes into flexion the tibio-femoral contact area decreases and hence contact stress increases. Tibio-femoral conformity is the ratio of the femoral radius to the tibial radius in the medial-lateral plane and in the anterior-posterior plane. Thus, medial-lateral conformity can be expressed as $$\frac{R_{fM/L}}{R_{iM/L}}$$

where $R_{fM/L}$ is the femoral radius in the medial-lateral plane and $R_{iM/L}$ is the tibial insert radius measured in the medial-lateral plane. Similarly, conformity in the anterior-posterior plane, or anterior-posterior conformity, can be expressed as $$\frac{R_{fA/P}}{R_{iA/P}}$$

Where $R_{fA/P}$ is the femoral radius in the anterior-posterior plane and $R_{iA/P}$ is the tibial radius in the anterior-posterior plane. A decrease in conformity between the two components results in a decrease in contact area and an increase in contact stress.

Conformity can be measured at any flexion angle. Generally, the anterior-posterior conformity of existing knee prostheses decreases as the femoral component rotates into flexion. This results from a decrease in the femoral radius in the sagittal plane at higher flexion angles, due to anatomic constraints. In the present invention, the decrease in anterior-conformity posterior conformity is offset by an increase in medial-lateral conformity. This is accomplished by gradually increasing the coronal radii of the bearing surface 23 of condyles 20, 22 from anterior to posterior portions of the bearing surface 23 of condyles 20, 22. The increasing coronal radius (in the Medial-lateral direction) results in an increase in medial-lateral conformity. This increase in medial-lateral conformity causes the tibio-femoral contact area to remain more stable (i.e., to remain constant or to decrease to a lesser extent) as compared to representative existing knee joint prostheses.

FIG. 3 illustrates the curvature of bearing surface 23 of condyles 20, 22 lying in the coronal plane and extending in the medial-lateral direction at a point on the bearing surface corresponding to approximately 0° flexion. The curvature at this point on the bearing surface is defined by the initial coronal radius ($R_{c(i)}$). Preferably, the initial coronal radius is in the range of about 0.70 to 1.1 inches. The value of the coronal radius, as noted above, increases gradually from the initial coronal radius as one moves along the bearing surface 23 from this anterior portion of the articulation surface to posterior portions of the articulation surface. Generally, the coronal radius increases by approximately 4 to 7% from the $R_{c(i)}$ to a point on the bearing surface corresponding to flexion of approximately 90°.

Figure 6:
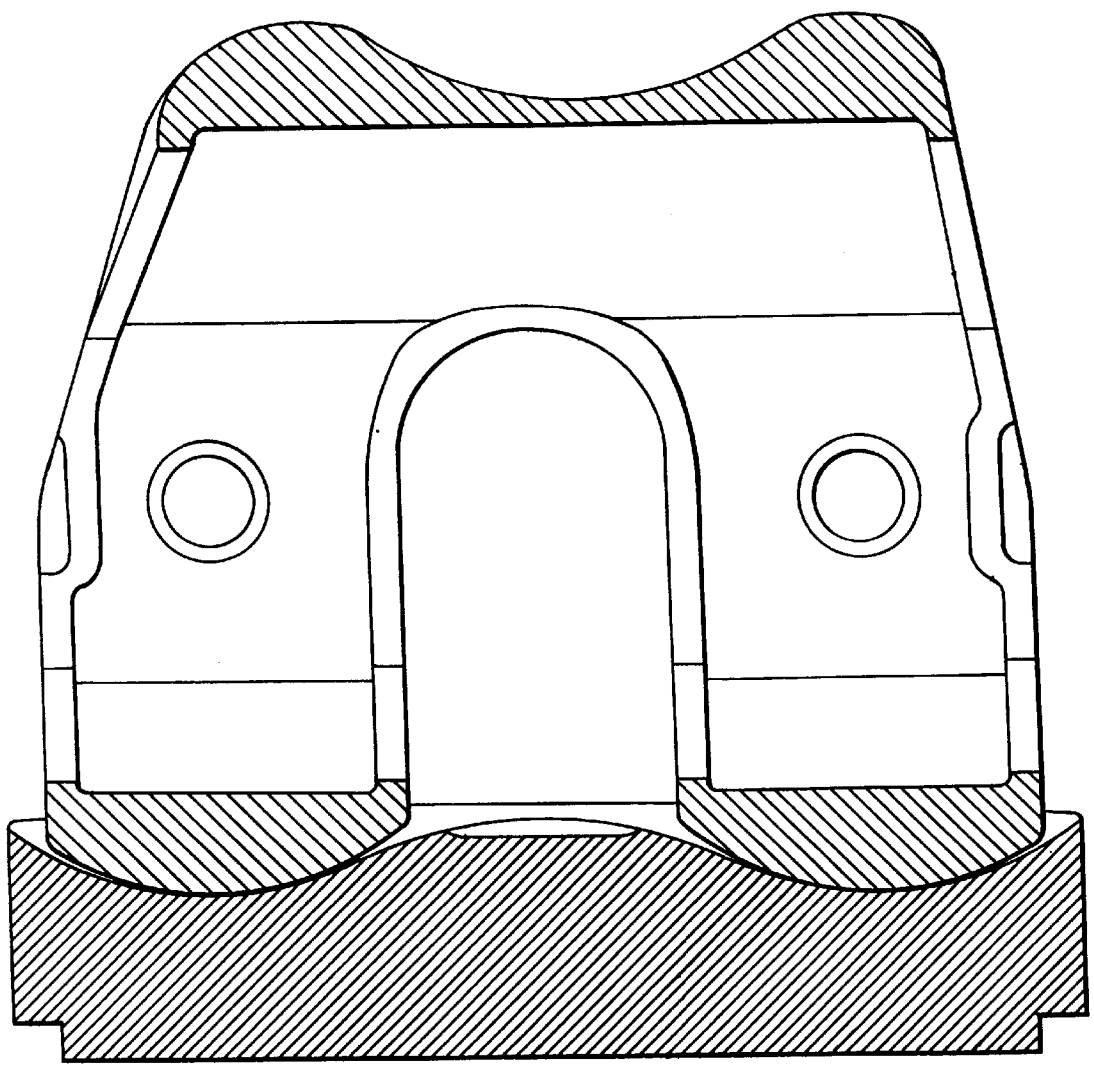
FIG. 6 is a partial sectional view at lines 6—6, in the coronal plane, of the femoral component illustrated in FIG. 2.
Figure 7:
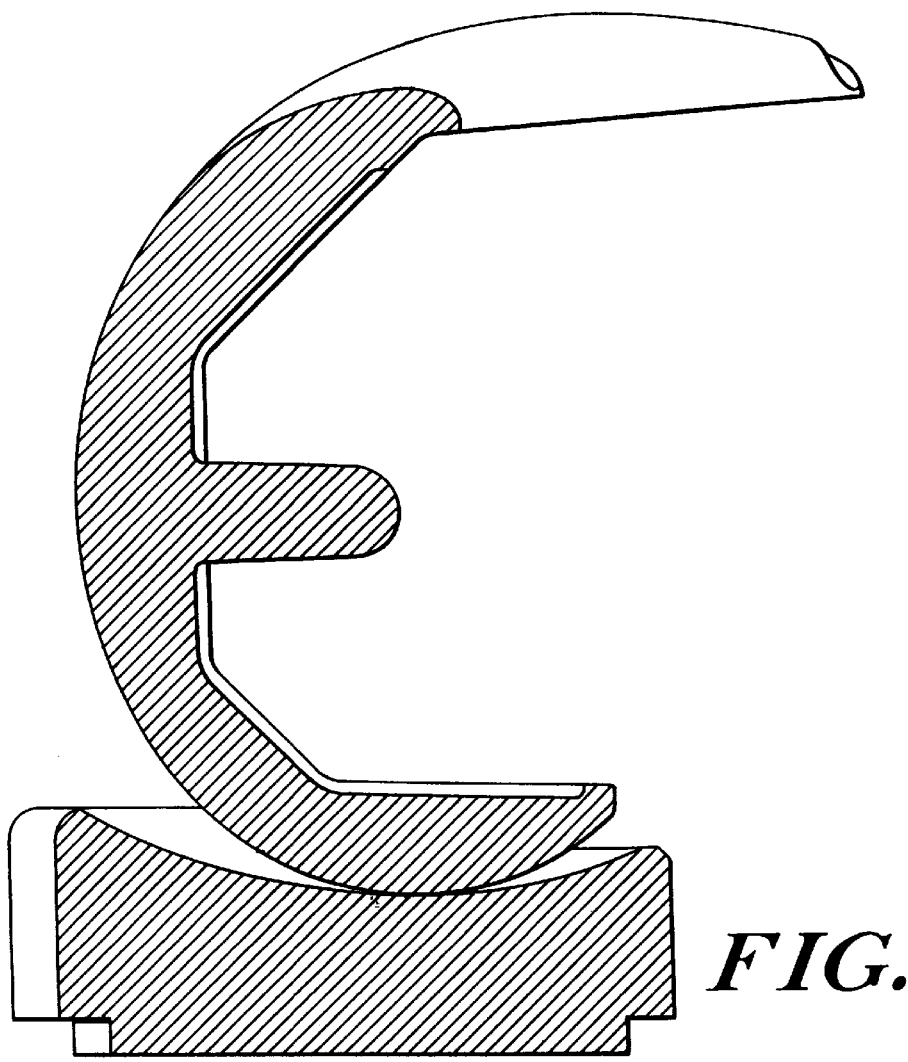
FIG. 7 is a side view (from the medial side) of the femoral component of the present invention mounted adjacent to a tibial bearing member at 90° flexion.

FIG. 6 illustrates the curvature of the bearing surface 23 of condyles 20, 22 lying in the coronal plane and extending in the medial-lateral direction at a point on the bearing surface 23 corresponding to approximately 90° flexion. The value of the coronal radius at this point on the articulation surface preferably is in the range of about 0.74 to about 1.17 inches, and most preferably is about 0.848 inch. In a preferred embodiment, the coronal radius is independent of the size of the femoral component or tibial bearing member used in the joint prosthesis.

Referring again to FIGS. 1 through 7, tibial bearing member 34 includes adjacent lateral 42 and medial 44 tibial condylar elements that are generally ellipsoid and are configured to seat and articulate with condyles 20, 22 of femoral component 12. The tibial condylar elements 42, 44 preferably are of a curved, concave shape. The articulation surface 40 of tibial condylar elements 42, 44 is characterized by a curved, concave surface in both the medial-lateral and anterior-posterior directions. The curvature of the tibial condylar elements 42, 44 lying in the sagittal plane and extending in the anterior-posterior direction is defined by a sagittal radius ($R_S$). Preferably, this radius is approximately 120% to 152% of the first sagittal radius ($R_1$) of the condylar elements 20, 22 of femoral component 12.

The curvature of the condyles 42, 44 of the tibial bearing member 34 lying in the coronal plane and extending in the medial-lateral direction is defined by a coronal radius ($R_c$).

The coronal radius of the condyles 42, 44 of the tibial bearing member preferably is approximately 104% to 120% of the initial coronal radius $R_{c(i)}$ of the condyles 20, 22 of the femoral component 12.

The knee joint prosthesis 10 of the present invention provides many advantages. As noted above, the tibial-femoral contact area is improved and contact stress is reduced. A major improvement in contact area is evident during flexion. While many knee joint prostheses experience dramatic decrease in tibio-femoral contact area during flexion (on the order of about 40%), the present knee prosthesis is less susceptible to dramatic decreases in tibio-femoral contact area.

Figure 8:
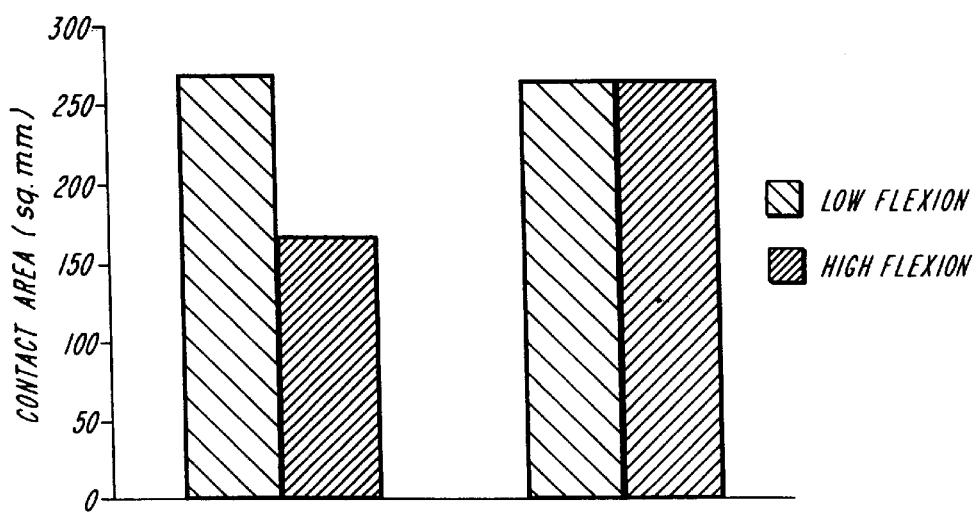
FIG. 8 is a bar graph comparing contact area at high and low flexion angles for knee joint prostheses according to the present invention and prior art knee joint prostheses.

FIG. 8 compares predicted contact area for knee joint prostheses made according to a representative existing design and the present invention (varying coronal radius condyle design) at low flexion (about 15°) through high flexion (about 90°).

The data was generated using as a sample a medium size representative existing design (i.e., P.F.C. Knee System available from Johnson & Johnson Professional, Inc.) and a knee joint prosthesis constructed according to the present invention. The knee joint prosthesis constructed according to the present invention was a medium size prosthesis having a minimum and maximum femoral condyle radii of 0.800 to 0.832 inches, respectively.

Data was generated both through theoretical and experimental methods as follows. Contact stress and contact area were calculated using an approximate elasticity solution to the rigid indenter (femoral condyles) on an elastic bearing surface (tibial insert) problem. This method was adapted from that developed and used by Bartel and his coworkers to investigate the effects of geometry and material properties on contact stress in joint arthroplasty components. (See, Bartel et al., *J Biomech. Eng.*, Vol. 107, August 1985, pp. 193–199; Bartel, et al., *JBJS*, Vol. 68-A, No. 7, September 1986, pp. 1041–1051.) Bartel et al. concluded from their investigation that the elasticity solution was valid for use in parameter studies. The load applied during this procedure was 450 pounds. The method has also been shown to be valid for comparative purposes using Tekscan measurement of stress and area as a baseline. The ratio of peak stress to average stress of 1.5 (i.e., peak stress=1.5 times average stress) as given by Hertzian contact theory has also been shown to agree well with measured and calculated force, area and stress data. (See, Timoshenko et al., *Theory of Elasticity*, 3rd Edition, McGraw-Hill, New York, 1970, Reissue, 1987.) The experimental data are illustrated in FIG. 8.

As shown in FIG. 8 the current femoral condyle design with multiple, increasing coronal radii achieves substantially constant contact area at low and high flexion. In contrast, conventional designs exhibit a dramatic decrease in contact area from low to high flexion conditions.

Figure 9:
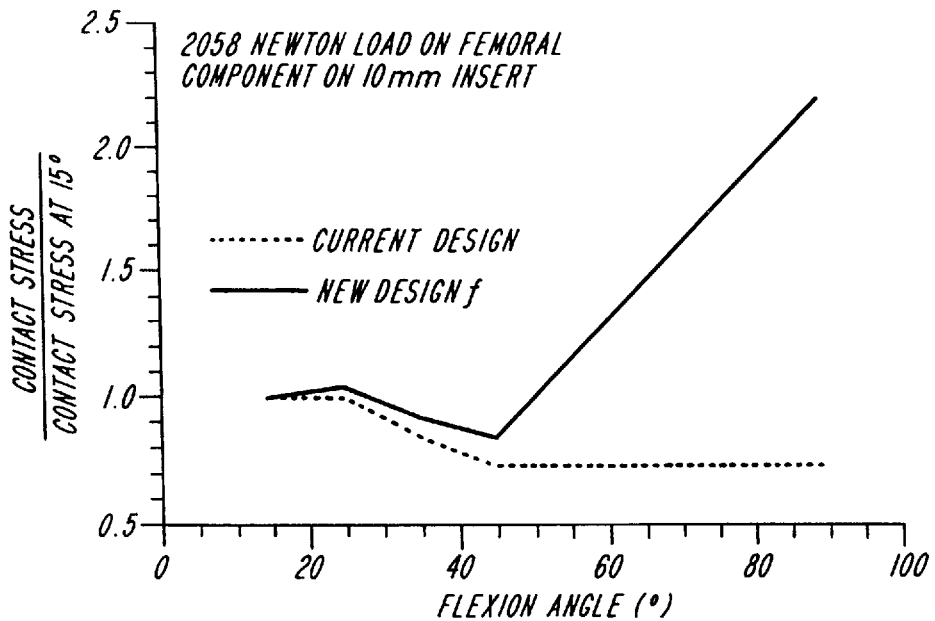
FIG. 9 is a graph comparing the ratio of contact area through the range of motion to contact area at 15° flexion plotted against flexion angle for knee joint prostheses according to the present invention and prior art knee joint prostheses.
Figure 10:
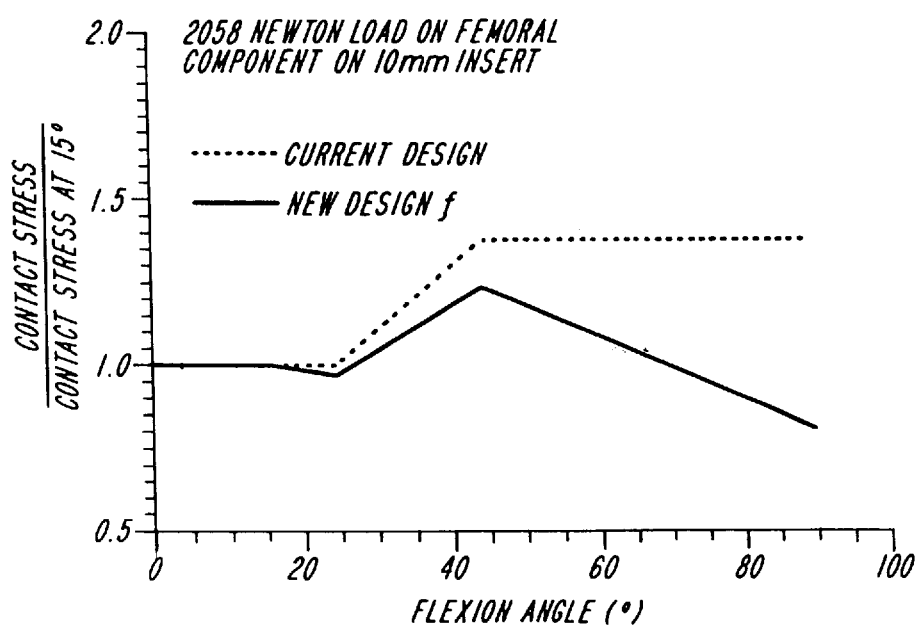
FIG. 10 is a graph comparing the ratio of contact stress through the range of motion to contact stress at 15° flexion plotted against flexion angle for knee joint prosthesis according to the present invention and prior art knee joint prostheses.

FIGS. 9 and 10 illustrate data obtained by plotting the ratio of contact area to contact area at 15° flexion versus flexion angle (FIG. 9) and contact stress to contact area at 15° flexion versus flexion angle (FIG. 10) for both the current design and a conventional design.

The data were developed using the knee joint prostheses described above with respect to FIG. 8, and the procedure for obtaining the data is similar to that described for FIG. 8.

The design and geometry of the articulation surfaces of the femoral component and tibial bearing member of the knee prostheses made according to the present invention lends itself to use with a variety of different constructions for a knee joint prosthesis. That is, the articulation surface design and geometry described herein may be incorporated to knee joint prostheses such as cruciate retaining knee prostheses, cruciate sacrificing knee prostheses, meniscal bearing prostheses, revision prostheses, hinge prostheses, and unicondylar prostheses.

It will be appreciated by those of ordinary skill in art that the knee prostheses of the invention can be made from a variety of biocompatible materials having high strength, durability and resistance to wear debris. Examples of such materials include metal alloys such as cobalt-chromium alloy, titanium-aluminum-vanadium alloy, stainless steel, ceramics, and other materials that are well known for use in the manufacture of implantable bone prostheses. Typically, the femoral component and tibial plateau are made from metal alloys such as cobalt-chromium alloy while the tibial bearing member is made from polymers such as ultra-high molecular weight polyethylene.

The foregoing description of the invention is presented to indicate the range of constructions to which the invention applies. Variations in the physical architecture and dimensions of the knee prostheses will be apparent to those having ordinary skill in the art based upon the disclosure herein and such variations are considered to be within the scope of the invention in which patent rights are asserted, as set forth in the claims appended hereto.

The entirety of all references cited herein is expressly incorporated by reference.

What is claimed is:

1. A knee joint prosthesis, comprising:
   a femoral component having an inferior surface mountable on a distal end of a femur of a patient and a superior articulation surface including two adjacent, semi-parallel bearing surfaces, each bearing surface being of a curved, convex shape in both an anterior-posterior direction and in a medial-lateral direction, wherein a curvature of each bearing surface lying in a coronal plane and extending in the medial-lateral direction is defined by multiple coronal radii, wherein the coronal radii increase in value along the bearing surface from an anterior portion of the bearing surface to a posterior portion of the bearing surface;
   a tibial component having a proximal end and a distal end mountable on the tibia of a patient; and
   a tibial bearing member having a distal surface mountable within the proximal end of the tibial component and a proximal articulation surface, the proximal articulation surface including adjacent tibial condylar elements that seat adjacent, semi-parallel bearing surfaces of the femoral component.

2. (Amended) The prosthesis of claim 1 wherein the tibial condylar elements of the tibial bearing member are each of a curved, concave shape in both anterior-posterior and medial-lateral directions and a curvature of the tibial condylar elements lying in a coronal plane and extending in a medial-lateral direction is defined by a tibial coronal radius.

3. The prosthesis of claim 2 wherein the curvature of each bearing surface lying in a sagittal plane, in contact with a tibial condylar element, and extending in the anterior-posterior direction is defined by at least two semi-parallel radii wherein a first sagittal radius is more anterior than a second sagittal radius, with the first and second sagittal radii being offset from one anther by a distance between their respective centers of curvature.

4. The prosthesis of claim 2 wherein the coronal radii increase from a minimum radius value at an anterior-most point on the bearing surface in contact with the condylar elements of the tibial bearing member at about 0° flexion to a maximum radius value at a posterior-most point on the bearing surface in contact with the condylar elements of the tibial bearing member corresponding to about 90° flexion.

5. The prosthesis of claim 4 wherein the coronal radii remain substantially constant beyond the maximum radius value at a posterior-most point on the bearing surface in contact with the condylar elements of the tibial bearing member corresponding to about 90° flexion.

6. The prosthesis of claim 4 wherein the coronal radii increase by approximately 4 to 7 percent from the minimum radius value to the maximum radius value.

7. The prosthesis of claim 4 wherein the minimum radius value is in the range of about 0.7 to 1.1 inches.

8. The prosthesis of claim 4 wherein the maximum radius value is in the range of about 0.74 to about 1.17 inches.

9. The prosthesis of claim 4 wherein the maximum radius value is less than or equal to the tibial coronal radius value.

10. The prosthesis of claim 4 wherein the maximum radius value is approximately 2% less than the value of the tibial coronal radius.

11. The prosthesis of claim 4 wherein the coronal radii range from a minimum value of about 0.80 inch to a maximum value of about 0.85 inch.

12. The prosthesis of claim 3 wherein the tibio-femoral contact area of the prosthesis remains substantially the same throughout a range of motion of the prosthesis from 0° flexion to about 90° flexion.

13. The prosthesis of claim 12 wherein the tibio-femoral contact area is in the range of about 200 to 400 mm$^2$ throughout the range of motion of the knee joint prosthesis from 0° flexion to about 90° flexion.

14. A knee joint prosthesis, comprising:

a femoral component having an inferior surface mountable on a distal end of a femur of a patient and a superior articulation surface including at least one bearing surface that is of a curved, convex shape in both an anterior-posterior direction and in a medial-lateral direction, wherein a curvature of the bearing surface lying in a coronal plane and extending in a medial-lateral direction is defined by multiple coronal radii, wherein the coronal radii increase in value from an anterior portion of the bearing surface to a posterior portion of the bearing surface; and a tibial component having means for mounting upon a tibia of a patient and an articulation surface including at least one tibial condylar element that seats the bearing surface of the femoral component.

* * * * *